US007741366B2

United States Patent
Mackles et al.

(10) Patent No.: US 7,741,366 B2
(45) Date of Patent: Jun. 22, 2010

(54) LOW PH PHARMACOLOGICALLY ACTIVE PRODUCTS AND METHODS FOR THE PRODUCTION THEREOF

(76) Inventors: Leonard Mackles, 311 E. 23rd St., New York, NY (US) 10010; William Bess, 31 Greenwich Rd., Edison, NJ (US) 08820

(*) Notice: Subject to any disclaimer, the term of this patent is extended or adjusted under 35 U.S.C. 154(b) by 320 days.

(21) Appl. No.: 11/626,551

(22) Filed: Jan. 24, 2007

(65) Prior Publication Data

US 2008/0089914 A1    Apr. 17, 2008

Related U.S. Application Data

(60) Provisional application No. 60/828,984, filed on Oct. 11, 2006.

(51) Int. Cl.
*A61K 31/19*    (2006.01)
*A61K 31/201*    (2006.01)
*A61K 31/34*    (2006.01)
*A61K 31/60*    (2006.01)
*A61K 47/02*    (2006.01)

(52) U.S. Cl. .................. 514/557; 514/159; 514/474; 514/560; 514/769

(58) Field of Classification Search ............... None
See application file for complete search history.

(56) References Cited

U.S. PATENT DOCUMENTS 6,120,756 A * 9/2000 Markowitz ............... 424/70.1
2004/0062735 A1* 4/2004 Sun et al. ................. 424/70.1

OTHER PUBLICATIONS

STN online, file BIOSIS, Acc. No. 1945:10947, Doc. No. PREV19451900011002 (Keeney et al., Bull. Johns Hopkins Hosp. (1994), vol. 75, No. 6, pp. 377-392), Abstract.*

* cited by examiner

*Primary Examiner*—Johann R Richter
*Assistant Examiner*—Frank I Choi
(74) *Attorney, Agent, or Firm*—Omri M. Behr

(57) ABSTRACT

There is provided a new technology that will allow the formulation of pharmaceutically active organic acid products at relatively high pH during storage. This affords the advantages of avoiding formulation with the acid form of the product, yet when the product is used, the pH will be reduced via a chemical reaction, thus forming the organic acid which is the active form of the product. A by-product of the reaction is a significant increase in temperature, thus adding to the efficacy of the organic acid.

35 Claims, No Drawings

LOW PH PHARMACOLOGICALLY ACTIVE PRODUCTS AND METHODS FOR THE PRODUCTION THEREOF

RELATED APPLICATIONS

This application claims priority of provisional application 60/828,984 filed Oct. 11, 2006.

FIELD OF THE INVENTION

Low pH pharmacologically active products

BACKGROUND OF THE INVENTION

Organic acids are widely used in personal care products to treat a number of skin conditions. Examples include, salicylic acid for treatment of acne vulgaris, lactic or glycolic acid for treatment of dry skin, and undecylenic acid for athlete's foot. However, use of these acids in their acidic form often presents specific problems with product stability, interaction with packaging materials, fragrance interactions, solubility issues, off-odor issues, etc.

Related Prior Art

U.S. Pat. No. 3,341,418 discloses a two-part aqueous composition in which the parts are mixed just prior to or during use with evolution of heat. One part of the composition contains an oxidizing agent and the other part a reducing agent. These compositions are used for skin and hair care preparations, and in particular for shaving preparations.

U.S. Pat. No. 4,011,878 discloses a process for permanently waving hair using a self-heating composition containing two aqueous components, one with a water-soluble sulfite, metabisulfite or bisulfite, and thiourea and the other component containing hydrogen peroxide. The two components are mixed prior to use with evolution of heat.

U.S. Pat. No. 6,287,580 discloses a self-heating cosmetic composition that includes a skin conditioning agent and redox system based on iron powder (e.g. elemental iron, iron oxides, and ferrous salts) and a high surface area catalyst. The compositions are taught in different forms such as lotions, creams, ointments emulsions, etc. The system is activated by contact with moisture and air.

US Pat. Application 2004/0062798 discloses a composition containing at least one oxidizing agent and at least one reducing agent, wherein the equivalent ratio of the at least one oxidizing agent to the at least one reducing agent is greater than 1:1, and the article is exothermic when wet with water, and the use thereof to whiten at least one tooth.

While the redox reaction between hydrogen peroxide and various reducing agents is well known, none of the prior art discloses, nor suggests, the use of the reaction between metabisulfites and peroxide as a means of generating organic acids from organic acid salts.

SUMMARY OF THE INVENTION

The present invention discloses a new technology that will allow the formulation of products at relatively high pH during storage thus affording the advantages of not formulating with the acid form of the compound, yet when the product is used, the pH will be reduced via a chemical reaction, thus forming the organic acid which is the active form of the compound. In addition, a by-product of the reaction is a significant increase in temperature, thus adding to the efficacy of the organic acid by increasing its ability to react with the skin, or microbes on the skin.

DESCRIPTION OF THE PREFERRED EMBODIMENTS

The present invention utilizes a dual phase oxidation-reduction reaction between reducing salts such as salts in one phase (phase or solution A) and hydrogen peroxide or a hydrogen peroxide generating compound. Examples of the latter include but are not limited to carbamide peroxide potassium persulfate or sodium perborate or combinations thereof, in the other (phase or solution B) phase, in combination with the salt of an organic acid in at least one of the phases though its presence in phase A is preferred. The cations of the peroxide generating salts include but are not limited to sodium, potassium, ammonium, iron, magnesium, calcium, amine compounds and combinations thereof.

Among reducing salts, there are suitably used metabisulfites or hydrosulfites or combinations thereof. The presence of a sulfite as an auxiliary heat generating reducing agent has also been found useful. They may be salts of cations including but not limited to sodium, potassium, ammonium, iron, magnesium, calcium, amine compounds and combinations thereof.

The amount of metabisulfites and hydrosulfites, relative by weight of the phase A composition, as well as that of sulfites when employed, may vary between 0.1 and 20 wt % though in the especially preferred foam compositions of the present invention it will generally lie between 10 and 20 wt %. The actual amount specified will vary in accordance with several factors. These include but are not limited to the amount of heat desired when the two phases are mixed, the concentration of organic acid salt present in the formulation, the final desired pH of the mixed phases and the specific cation used in the formulation. It should be noted that other ingredients in the formulation may also affect the pH, heat formation or solubility of the aforementioned reducing salts.

A substantial range of organic acids having pharmacological activity are made usefully available by means of in the present invention. Among these acids, which are listed for the purpose of exemplification rather than limitation there may be named alpha hydroxyl acids such as lactic, glycolic and citric acids whose salts would comprise from 0.1-20 wt % preferably 1-10 wt % of the, suitably, phase A formulation.

Among the other acid salts which are useful in the present invention are those of salicylic acid whose salts would comprise from 0.1-25 wt %, suitably 0.1-20 wt % preferably 0.5-5 wt % of the, suitably, phase A formulation; undecylenic acid whose salts would comprise from 0.1-25 wt %, suitably 0.1-20 wt %, preferably 5-20 wt % of the, suitably, phase A formulation; ascorbic acid whose salts would comprise from 0.1-20 wt % suitably 0.1-15 wt % preferably 1-10 wt % of the, suitably, phase A formulation and benzoic acid whose salts would comprise from 0.1-5 wt % preferably 1-3 wt % of the, suitably, phase A formulation.

Among salts of these acids there may be mentioned the salts of cations including but not limited to sodium, potassium, ammonium, iron, magnesium, calcium, amine compounds and combinations thereof.

The actual amount of acid salt specified will vary in accordance with several factors. These include but are not limited to the solubility of organic acid salt used, its compatability with other ingredients, the skin condition being treated and the specific cation used in the formulation.

Any suitable source of peroxide may be employed. Water soluble peroxides are preferred and hydrogen peroxide is especially desirable. While not limited thereto aqueous hydrogen peroxide in particular 50 wt % aqueous hydrogen peroxide is generally employed. A Solution B containing between 5 and 15 wt % of 50 wt % aqueous hydrogen peroxide has been found useful.

When the reducing salt, such as metabisulfite or hydrosulfite is combined with hydrogen peroxide, the reducing salt is oxidized to bisulfate, which is highly acidic, the pH of the solution is substantially reduced and in the presence of an organic acid salt, will form the organic acid, by shifting the equilibrium between salt and acid towards the acid.

By way of example only, salicylic acid, which is used as an active ingredient in anti-acne products, is water insoluble in its acid form. Products formulated with salicylic acid must then either utilize suspending agents to insure a stable suspension of salicylic acid, or must use large amounts of auxiliary compounds to solubilize it. Using the technology disclosed in the present invention, a solution of sodium salicylate is utilized, which is then converted to salicylic acid when the product is used. Undecylenic acid, which is used in antifungal products, has an unpleasant odor in the acid form. This odor is greatly reduced in the salt form that can be used in the present invention. Thus it would be advantageous to formulate products with the salts of organic acids where these issues would not be present.

The following is the reaction between Sodium Metabisulfite and Hydrogen Peroxide showing the change in pH.

$$Na_2S_2O_5 + 2H_2O_2 = 2NaHSO_4 + H_2O$$

1M Sol'n pH = 3.7  2M Sol'n pH = 3.5  (2M Sol'n pH = <0.5)

Clearly, the final product pH may be adjusted higher to optimize the consumer appeal of the product. Towards that end, by way of example only, inorganic bases such as sodium hydroxide, or potassium carbonate can be utilized to adjust the final pH. Alternatively, alkaline salts such as sodium sulfite, or sodium tripolyphosphate can be added to buffer the final pH. Similarly, organic amines such as triethanolamine, trisamine, or isopropanolamine can be utilized as well. It will be appreciated by those skilled in the art, that these compositions may include other ingredients that are normally employed in topical formulations. Non-limiting examples would include thickeners, opacifiers, antimicrobial agents, emulsifiers, emollients, fragrances, gelling agents, co-solvents, surfactants, alcohols, glycols, silica, talc, coloring agents and the like. The present invention can be utilized to prepare final products in any consumer acceptable dosage form. Non-limiting examples include lotions, creams, foams, gels, and sprays.

EXAMPLES

Example 1

AntiAcne Lotion

|  | % wt |
| --- | --- |
| Phase A | |
| Sodium Metabisulfite | 15.00 |
| Sodium Salicylate | 2.30 |
| Glycerin | 10.00 |
| Water | 61.70 |
| NaOH (50%) | 11.00 |
| Total | 100.00 |
| pH Phase A = 7.9 | |

|  | % wt |
| --- | --- |
| Phase B | |
| Hydrogen Peroxide (50%) | 10.80 |
| Water | 89.20 |
| Total | 100.00 |
| pH Phase B = 4.3 | |

Combine equal volumes of Phase and Phase B prior to applying to skin.
pH of combined lotion = 2.9

Example 2

Skin Conditioning Foam

|  | % wt |
| --- | --- |
| Phase A | |
| Sodium Metabisulfite | 15.00 |
| Sodium Lactate | 8.40 |
| Cocamidopropyl betaine 30 wt % aq | 10.00 |
| Glycerin (99 wt % aq) | 10.00 |
| Water | 45.60 |
| NaOH (50%) | 11.00 |
| Total | 100.00 |
| pH Phase A = 7.3 | |
| Phase B | |
| Hydrogen Peroxide (50%) | 10.80 |
| Poloxamer 407 (10%) | 25.00 |
| Water | 64.20 |
| Total | 100.00 |
| pH Phase B = 4.3 | | pH of combined foam product = 4.2
Use with Airspray Dual Foamer (Airspray International Inc. 1-954-972-7750)

Example 3

AntiAcne Foam

|  | % wt |
| --- | --- |
| Phase A | |
| Sodium Metabisulfite | 1.00 |
| Sodium sulfite | 14.00 |
| Sodium Salicylate | 4.60 |
| Cocamidopropyl betaine 30 wt % aq | 10.00 |
| Glycerin | 15.00 |
| Water | 55.40 |
| Total | 100.00 |
| pH Phase A = 7.4 | |

-continued

|  | % wt |
|---|---|
| Phase B | |
| Hydrogen Peroxide (50%) | 9.00 |
| Poloxamer 407 (10%) | 25.00 |
| Water | 66.00 |
| Total | 100.00 |
| pH Phase B = 4.3 | |

Combine equal volumes of Phase A and Phase B prior to applying to skin.
pH of combined foam = 3.3
Use with Airspray Dual Foamer (Airspray International Inc. 1-954-972-7750)

Example 4

Skin Conditioning Foam

|  | % wt |
|---|---|
| Phase A | |
| Sodium Metabisulfite | 1.00 |
| Sodium sulfite | 14.00 |
| Sodium Lactate | 8.40 |
| Cocamidopropyl betaine 30 wt % aq | 10.00 |
| Glycerin | 15.00 |
| Water | 51.60 |
| Total | 100.00 |
| pH Phase A = 7.5 | |
| Phase B | |
| Hydrogen Peroxide (50%) | 9.00 |
| Poloxamer 407 (10%) | 25.00 |
| Water | 66.00 |
| Total | 100.00 |
| pH Phase B = 4.3 | |

Combine equal volumes of Phase A and Phase B prior to applying to skin.
pH of combined foam = 2.8
Use with Airspray Dual Foamer (Airspray International Inc. 1-954-972-7750)

Example 5

AntiFungal Foam

|  | % wt |
|---|---|
| Phase A | |
| Sodium Metabisulfite | 1.00 |
| Sodium sulfite | 14.00 |
| Sodium Undecylenate | 4.60 |
| Cocamidopropyl betaine 30 wt % aq | 10.00 |
| Glycerin | 15.00 |
| Water | 55.40 |
| Total | 100.00 |
| pH Phase A = 7.4 | |

-continued

|  | % wt |
|---|---|
| Phase B | |
| Hydrogen Peroxide (50%) | 9.00 |
| Poloxamer 407 (10%) | 25.00 |
| Water | 66.00 |
| Total | 100.00 |
| pH Phase B = 4.3 | |

Combine equal volumes of Phase A and Phase B prior to applying to skin.
pH of combined foam = 3.3
Use with Airspray Dual Foamer (Airspray International Inc. 1-954-972-7750)

Example 6

Vitamin C Foam for Skin

|  | % wt |
|---|---|
| Phase A | |
| Sodium Metabisulfite | 1.00 |
| Sodium sulfite | 14.00 |
| Sodium Ascorbate | 1.00 |
| Cocamidopropyl betaine 30 wt % aq | 10.00 |
| Glycerin | 15.00 |
| Water | 59.00 |
| Total | 100.00 |
| pH Phase A = 7.3 | |
| Phase B | |
| Hydrogen Peroxide (50%) | 9.00 |
| Poloxamer 407 (10%) | 25.00 |
| Water | 66.00 |
| Total | 100.00 |
| pH Phase B = 4.3 | |

Combine equal volumes of Phase A and Phase B prior to applying to skin.
pH of combined foam = 3.0
Use with Airspray Dual Foamer (Airspray International Inc. 1-954-972-7750)

Example 7

AntiAcne Lotion

|  | % wt |
|---|---|
| Phase A | |
| Sodium Metabisulfite | 15.00 |
| Glycerin | 10.00 |
| Water | 64.00 |
| NaOH (50%) | 11.00 |
| Total | 100.00 |
| pH Phase A = 7.9 | |

-continued

| | % wt |
|---|---|
| Phase B | |
| Sodium Salicylate | 2.30 |
| Hydrogen Peroxide (50%) | 10.80 |
| Water | 86.90 |
| Total | 100.00 |
| pH Phase B = 4.3 | |

Combine equal volumes of Phase and Phase B prior to applying to skin.
pH of combined lotion = 2.9

Example 8

Skin Conditioning Foam

| | % wt |
|---|---|
| Phase A | |
| Sodium Metabisulfite | 15.00 |
| Cocamidopropyl betaine 30 wt % aq | 10.00 |
| Glycerin (99 wt % aq) | 10.00 |
| Water | 54.00 |
| NaOH (50%) | 11.00 |
| Total | 100.00 |
| pH Phase A = 7.3 | |
| Phase B | |
| Sodium Lactate | 8.40 |
| Hydrogen Peroxide (50%) | 10.80 |
| Poloxamer 407 (10%) | 25.00 |
| Water | 55.80 |
| Total | 100.00 |
| pH Phase B = 4.3 | | pH of combined foam product = 4.2
Use with Airspray Dual Foamer (Airspray International Inc. 1-954-972-7750)

Example 9

In accordance with the procedures of Examples 1-8 above, in place of using sodium as the cation of the reducing salts or the acid salts there are utilized potassium, ammonium, iron, magnesium, calcium, amine compounds or combinations thereof, similar results are obtained.

Similarly, where in place of aqueous hydrogen peroxide, there utilized aqueous solutions of carbamide peroxide potassium persulfate or sodium perborate or combinations thereof, in place of the cations of the peroxide generating compounds mentioned above the cations of the peroxide generating salts include ammonium, iron, magnesium, calcium, amine compounds and combinations thereof whereby similar results are obtained.

We claim:

1. A method of providing an in situ prepared pharmacologically active organic acid comprising the step of mixing aqueous Solution "A" containing a salt of said organic acid in the presence of a reducing salt selected from the group consisting of metabisulfites, and hydrosulfites with Solution "B" containing an aqueous solution of a water soluble peroxide.

2. The method of claim 1 additionally comprising a water soluble sulfite in Solution A.

3. The method of claim 1 wherein the cationic portion of the salts of claim 1 is selected from the group consisting of sodium, potassium, ammonium, iron, magnesium, calcium, amine compounds and combinations thereof.

4. The method of claim 1 wherein the amount of the organic acid salt is between 0.1-25 wt % of Solution A and the amount of the reducing salt is between 0.1-20 wt % of Solution B.

5. The method of claim 4 wherein the amount of the reducing salt is between 10-20 wt % of Solution B.

6. The method of claim 1 wherein the organic acid is selected from the group consisting of alpha hydroxyl acids.

7. The method of claim 6 wherein the organic acid is selected from the group consisting of lactic, glycolic and citric acids.

8. The method of claim 6 wherein the amount of the organic acid salt is between 10-20 wt % of Solution A.

9. The method of claim 1 wherein the organic acid is selected from the group consisting of salicylic, ascorbic and undecylenic acids.

10. The method of claim 9 wherein the amount of the salicylic acid salt is between 0.5-5 wt % of Solution A.

11. The method of claim 9 wherein the amount of the undecylenic acid salt is between 5-20 wt % of Solution A.

12. The method of claim 9 wherein the amount of the ascorbic acid salt is between 1-10 wt % of Solution A.

13. The method of claim 1 wherein the peroxide is hydrogen peroxide.

14. The method of claim 1 wherein the peroxide is 50% aqueous hydrogen peroxide.

15. The method of claim 14 wherein the amount of the aqueous hydrogen peroxide is between 5 and 15 wt % of Solution B.

16. A method of providing an in situ prepared pharmacologically active organic acid comprising the step of mixing aqueous Solution "A" containing a reducing salt selected from the group consisting of metabisulfites, and hydrosulfites with Solution "B" containing an aqueous solution of a water soluble peroxide and a salt of said organic acid.

17. The method of claim 16 additionally comprising a water soluble sulfite in Solution A.

18. A kit for providing an in situ prepared pharmacologically active organic acid comprising:
    an aqueous Solution "A" containing a salt of said organic acid in the presence of a reducing salt selected from the group consisting of metabisulfites and hydrosulfites in the presence of a salt of said organic acid and
    Solution "B" containing an aqueous solution of a water soluble peroxide.

19. The kit of claim 18 wherein the cationic portion of the salts of claim 18 is selected from the group consisting of sodium, potassium, ammonium, iron, magnesium, calcium, amine compounds and combinations thereof.

20. The kit of claim 18 wherein the amount of the organic acid salt is between 0.1-25 wt % of Solution A and the amount of the reducing salt is between 0.1-20 wt % of Solution B.

21. The kit of claim 20 wherein the amount of the reducing salt is between 10-20 wt % of Solution B.

22. The kit of claim 18 wherein the organic acid is selected from the group consisting of alpha hydroxyl acids.

23. The kit of claim 22 wherein the organic acid is selected from the group consisting of lactic, glycolic and citric acids.

24. The kit of claim 22 wherein the amount of the organic acid salt is between 10-20 wt % of Solution A.

25. The kit of claim 18 wherein the organic acid is selected from the group consisting of salicylic, ascorbic and undecylenic acids.

26. The kit of claim 25 wherein the amount of the salicylic acid salt is between 0.5-5 wt % of Solution A.

27. The kit of claim 25 wherein the amount of the undecylenic acid salt is between 5-20 wt % of Solution A.

28. The kit of claim 25 wherein the amount of the ascorbic acid salt is between 1-10 wt % of Solution A.

29. The kit of claim 18 wherein the peroxide is hydrogen peroxide.

30. The kit of claim 18 wherein the peroxide is 50% aqueous hydrogen peroxide.

31. The kit of claim 30 wherein the amount of the aqueous hydrogen peroxide is between 5 and 15 wt % of Solution B.

32. A kit for providing an in situ prepared pharmacologically active organic acid comprising:
   an aqueous Solution "A" containing a reducing salt selected from the group consisting of metabisulfites and hydrosulfites and
   Solution "B" containing an aqueous solution of a water soluble peroxide in the presence of a salt of said organic acid.

33. An anti acne product prepared by the procedure of claim 10.

34. An anti fungal product prepared by the procedure of claim 11.

35. A skin care product prepared by the procedure of claim 12.

* * * * *